(12) United States Patent
Roeder et al.

(10) Patent No.: US 12,318,165 B2
(45) Date of Patent: Jun. 3, 2025

(54) SHEATHES FOR SURGICAL INSTRUMENTS, AND RELATED DEVICES AND METHODS

(71) Applicant: INTUITIVE SURGICAL OPERATIONS, INC., Sunnyvale, CA (US)

(72) Inventors: Jeffrey R. Roeder, Mountain View, CA (US); William J. Park, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 848 days.

(21) Appl. No.: 17/471,307

(22) Filed: Sep. 10, 2021

(65) Prior Publication Data

US 2021/0401530 A1     Dec. 30, 2021

Related U.S. Application Data

(62) Division of application No. 16/068,375, filed as application No. PCT/US2016/067705 on Dec. 20, 2016, now Pat. No. 11,129,687.

(Continued)

(51) Int. Cl.
    *A61B 46/10*     (2016.01)
    *A61B 17/34*     (2006.01)
    (Continued)

(52) U.S. Cl.
    CPC .......... *A61B 46/10* (2016.02); *A61B 17/3423* (2013.01); *A61B 34/35* (2016.02);
    (Continued)

(58) Field of Classification Search
    CPC ...... A61B 17/3423; A61B 2017/00477; A61B 2017/347; A61B 2034/306; A61B 34/35;
    (Continued)

(56) References Cited

U.S. PATENT DOCUMENTS 4,951,977 A    8/1990   Shutt
5,507,733 A    4/1996   Larkin et al.
(Continued)

FOREIGN PATENT DOCUMENTS

CN    102038998 A    5/2011
CN    102834062 A    12/2012
(Continued)

OTHER PUBLICATIONS

Extended European Search Report for Application No. 16884186.4 mailed on Jul. 17, 2019, 11 pages (ISRG06770/EP).
(Continued)

*Primary Examiner* — Scott Luan
(74) *Attorney, Agent, or Firm* — JONES ROBB, PLLC

(57) ABSTRACT

A sheath for a surgical instrument may include a sleeve having a distal end and proximal end, and a retention mechanism at a proximal end portion of the sleeve. The retention mechanism may comprise a sleeve attachment portion configured to be attached to the sleeve at the proximal end portion, and a locking collar extending from the sleeve attachment portion, wherein the locking collar is configured to receive a connector portion of a surgical instrument. The locking collar further may include a locking feature movable between a first configuration, in which the sheath is moveable relative to the surgical instrument, and a second configuration, in which the locking feature is configured to engage with the connector portion to retain the sheath in position on the surgical instrument.

20 Claims, 9 Drawing Sheets

Related U.S. Application Data

(60) Provisional application No. 62/276,471, filed on Jan. 8, 2016.

(51) Int. Cl.
*A61B 34/35* (2016.01)
*A61B 34/37* (2016.01)
*A61B 46/13* (2016.01)
*A61B 90/00* (2016.01)
*A61B 17/00* (2006.01)
*A61B 34/30* (2016.01)

(52) U.S. Cl.
CPC .............. *A61B 34/37* (2016.02); *A61B 46/13* (2016.02); *A61B 90/361* (2016.02); *A61B 2017/00477* (2013.01); *A61B 2017/347* (2013.01); *A61B 2034/306* (2016.02)

(58) Field of Classification Search
CPC ......... A61B 34/37; A61B 46/10; A61B 46/13; A61B 90/361
See application file for complete search history.

(56) References Cited

U.S. PATENT DOCUMENTS

| | | | |
|---|---|---|---|
| 6,817,974 B2 | 11/2004 | Cooper et al. |
| 8,852,208 B2 | 10/2014 | Gomez et al. |
| 9,089,351 B2 | 7/2015 | Park et al. |
| 11,129,687 B2 | 9/2021 | Roeder et al. |
| 2002/0072712 A1 | 6/2002 | Nool et al. |
| 2011/0251597 A1 | 10/2011 | Bharadwaj et al. |
| 2012/0283663 A1 | 11/2012 | Delegge |
| 2012/0310215 A1 | 12/2012 | Stout et al. |
| 2013/0267778 A1 | 10/2013 | Rehe |
| 2013/0325031 A1 | 12/2013 | Schena et al. |
| 2013/0325033 A1 | 12/2013 | Schena et al. |
| 2014/0171946 A1 | 6/2014 | Benson et al. |
| 2015/0080851 A1 | 3/2015 | Kurth et al. |
| 2015/0174372 A1 | 6/2015 | Kaiser |

FOREIGN PATENT DOCUMENTS

| | | |
|---|---|---|
| CN | 103945785 A | 7/2014 |
| EP | 2269523 A1 | 1/2011 |
| JP | S6218101 A | 1/1987 |
| JP | S6218101 U | 2/1987 |
| JP | H03101901 A | 4/1991 |
| JP | H03101901 U | 10/1991 |
| JP | H05208014 A | 8/1993 |
| JP | H06304118 A | 11/1994 |

OTHER PUBLICATIONS

International Search Report and Written Opinion for Application No. PCT/US2016/067705, mailed on Apr. 10, 2017, 14 pages (ISRG06770/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SHEATHES FOR SURGICAL INSTRUMENTS, AND RELATED DEVICES AND METHODS

This application is a divisional application of application Ser. No. 16/068,375, filed Jul. 6, 2018, which is a U.S. national phase of international application no. PCT/US2016/067705, filed Dec. 20, 2016, which designated the United States and claimed right of priority to U.S. provisional application No. 62/276,471, filed Jan. 8, 2016, each of which are incorporated herein by reference in their entirety.

TECHNICAL FIELD

Aspects of the present disclosure relate to protective sheaths for use with surgical instruments, and related devices and methods.

INTRODUCTION

Remotely controlled surgical instruments, which can include teleoperated surgical instruments (e.g., surgical instruments operated at least in part with computer assistance, such as instruments operated with robotic technology) as well as manually operated (e.g., laparoscopic, thorascopic) surgical instruments, are often used in minimally invasive medical procedures. During such procedures, a surgical instrument, which may extend through a cannula inserted into a patient's body, can be remotely manipulated to perform a procedure at a surgical site. For example, in a teleoperated surgical system (e.g., robotic surgical system), cannulas and surgical instruments can be mounted at manipulator arms of a patient side cart and may be remotely manipulated via teleoperation at a surgeon console.

The instruments employed during such procedures may be complex mechanical devices having many separate components (e.g., cables and mechanical members, such as joint and link structures. Accordingly, to reduce cost, it is desirable for the instruments to be reusable. However, reuse of a surgical instrument generally requires stringent cleaning and sterilization procedures that are made more difficult by the large number of small components and tight intervening spaces within such instruments.

To facilitate cleaning procedures for minimally invasive surgical instruments and/or reduce the cost per use of such instruments, sheaths have been used to cover the instrument shaft during use. It is desirable, however, to facilitate the installation and removal of sheaths on an instrument by surgical personnel. Further, it is desirable to provide sheaths that are relatively inexpensive to make, while providing robust attachment to the instruments to prevent accidental removal and/or repositioning relative to the instrument during use.

SUMMARY

Exemplary embodiments of the present disclosure may solve one or more problems and/or may demonstrate one or more desirable features, which will become apparent from the description that follows.

In accordance with various exemplary embodiments, a sheath for a surgical instrument may include a sleeve having a distal end and proximal end, and a retention mechanism at a proximal end portion of the sleeve. The retention mechanism may comprise a sleeve attachment portion configured to be attached to the sleeve at the proximal end portion, and a locking collar extending from the sleeve attachment portion, wherein the locking collar is configured to receive a connector portion of a surgical instrument. The locking collar further may include a locking feature movable between a first configuration, in which the sheath is moveable relative to the surgical instrument, and a second configuration, in which the locking feature is configured to engage with the connector portion to retain the sheath in position on the surgical instrument.

In accordance with further exemplary embodiments, a surgical instrument sheath assembly may include a surgical instrument comprising a shaft and a sheath connector portion, the shaft having a distal end configured to be introduced to a remote surgical site; a sheath sleeve configured to at least partially cover a shaft of a surgical instrument; and a sheath sleeve retention mechanism disposed at a proximal end portion of the sheath sleeve. At least one of the sheath sleeve retention mechanism and the sheath connector portion can include a movable locking feature, the movable locking feature having a first configuration allowing the sheath to be moved relative to the instrument and a second configuration engageably locking the sheath to the connector portion to retain the sheath sleeve in position to at least partially cover the instrument shaft.

In yet other exemplary embodiments, a method of assembling a protective sheath to a surgical instrument may include advancing the protective sheath over a distal working end of a surgical instrument shaft to a relatively proximally disposed sheath connector portion of the surgical instrument; moving a retention mechanism of the sheath into alignment with the sheath connector portion; and moving a moveable locking feature from a first configuration permitting the retention mechanism to be moved relative to the sheath connector portion to a second configuration in which complementary engagement features on the retention mechanism and the sheath connector portion are lockably engaged to retain the sheath in position on the instrument.

In further exemplary embodiments, a method of removing a protective sheath from a shaft of a surgical instrument may include applying a laterally inwardly directed force to a proximal end portion of retention mechanism to deform the proximal end portion from a first configuration to a second configuration, wherein in the first configuration, the retention mechanism is engaged with a connector portion of the instrument to retain a position of the sheath on the instrument, and in the second configuration retention mechanism is disengaged from the connector portion and the sheath is movable relative to the instrument. The method may further include moving the retention mechanism distally away from the connector portion to remove the sheath while the retention mechanism is in the second configuration.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

Both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
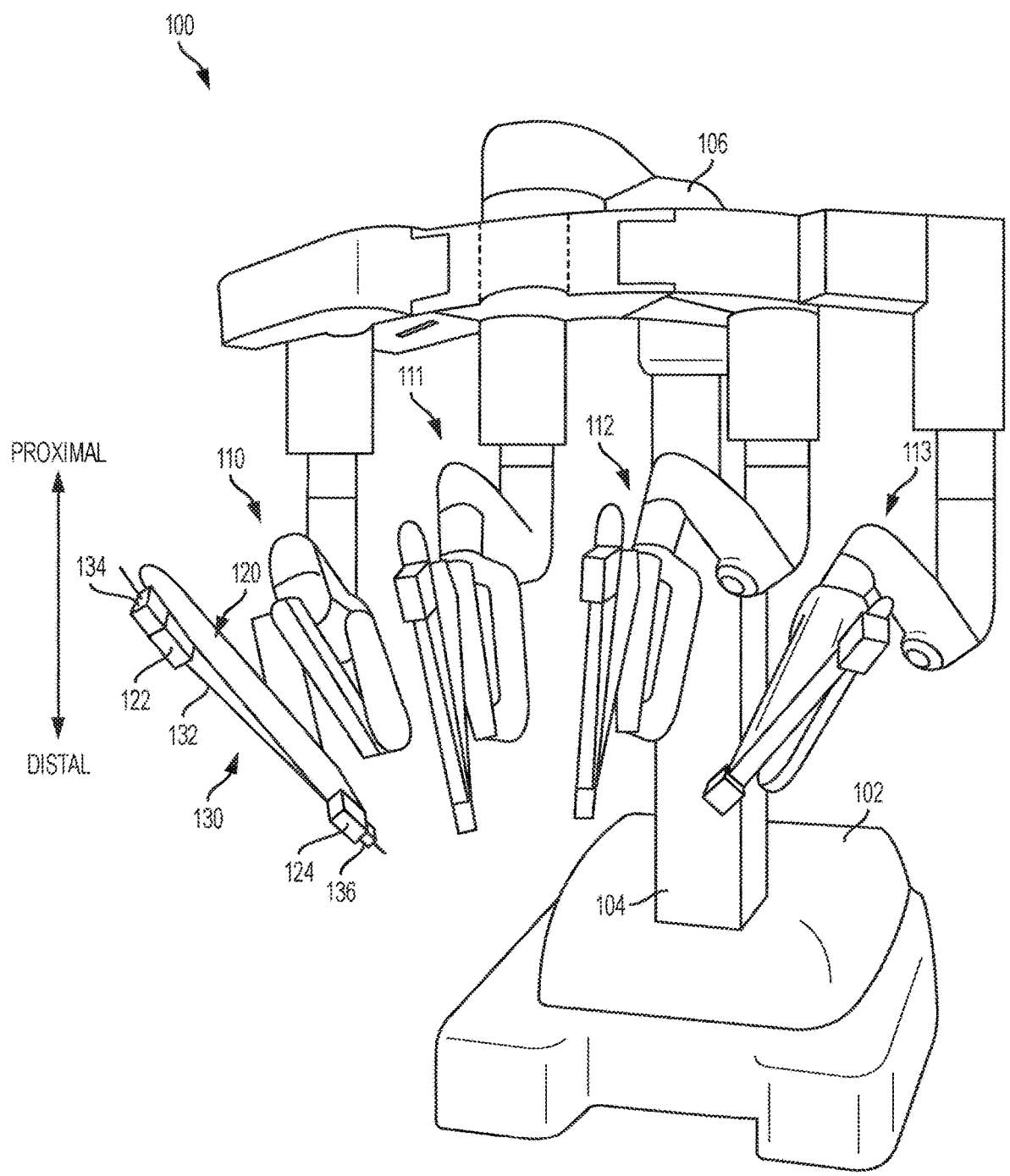
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative term-such as "top", "bottom", "lower", "above", "below", "upper", "proximal", "distal", and the like-may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates various surgical device sheaths, components of such sheaths, and methods of manufacturing such sheaths and associated components, systems, and methods of use. In accordance with an exemplary embodiment of the present disclosure, an instrument for minimally invasive surgical procedures employs a removable (e.g., replaceable) sheath to cover a shaft, wrist mechanism, and/or other joints and portions of the surgical instrument. The sheath may include a retention mechanism configured to engage with a corresponding (e.g., complementary) sheath connector portion (also "sheath connection portion") of a surgical instrument. Through the engagement, the retention mechanism may be configured to lock the sheath to the instrument to retain the sheath in position over at least a portion of a main shaft of the surgical instrument and/or at least a portion of a wrist mechanism of the surgical instrument during use of the instrument to perform a surgical procedure. The retention mechanism may be configured to facilitate manual placement and removal by an operator, such as a physician, nurse, and other operating room or hospital personnel. For example, in some exemplary embodiments, the retention mechanism may be configured to enable the sheath to be removed and installed with one hand.

In various exemplary embodiments, retention mechanisms may be configured to lockably engage with a connector portion of the instrument to prevent axial movement of the sheath relative to the instrument such that the sheath is prevented from being removed from the instrument in the absence of a force on the retention mechanism sufficient to unlock the sheath from engagement with the connector portion. Further, in various exemplary embodiments, retention mechanisms of the present disclosure may include anti-rotational features configured to prevent rotation of the sheath with respect to the surgical instrument when the sheath is in an assembled configuration (lockably engaged) on the surgical instrument. Such features may allow assembly of the sheath on the surgical instrument in any rotational orientation, or in a limited number of rotational orientations, the latter of which thus also allows the features to serve as rotational alignment mechanisms. In some embodiments, the corresponding sheath connector structure of the surgical instrument may not include any moving parts on the surgical instrument. Such an arrangement may enhance the reliability and robustness of the surgical instrument, and facilitate a user in assembly of the sheath and instrument. For example, for a surgical instrument that is designed to be reusable, exemplary embodiments provide sheath retention and connection designs that minimize the risk of parts of the instrument that relate to connection of the sheath failing and thus negatively impacting the ability to reuse the instrument.

The present disclosure also contemplates exemplary embodiments that use materials for the sheath, including the retention mechanism, that are relatively inexpensive and permit manufacturing via extrusion and/or molding, in addition to relatively inexpensive techniques to join the sheath sleeve body to the retention mechanism.

Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of sheaths for assembly with surgical instruments described herein can be used in conjunction with hand-held, manual surgical instruments.

Referring now to FIG. 1, an exemplary embodiment of a patient side cart 100 of a teleoperated surgical system is shown. A teleoperated surgical system may further include a surgeon console (not shown) for receiving input from a user to control instruments mounted at patient side cart 100. A teleoperated surgical system also can optionally include an auxiliary control/vision cart (not shown), as described in, for example, U.S. Pub. No. US 2013/0325033 A1, entitled "Multi-Port Surgical Robotic System Architecture" and published on Dec. 5, 2013, U.S. Pub. No. US 2013/0325031 A1, entitled "Redundant Axis and Degree of Freedom for Hardware-Constrained Remote Center Robotic Manipulator" and published on Dec. 5, 2013, and U.S. Pat. No. 8,852,208, entitled "Surgical System Instrument Mounting" and published on Oct. 7, 2014, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. However, those having ordinary skill in the art would appreciate that other surgical systems are contemplated as being used in conjunction with the sheaths and surgical instruments of the present disclosure, including for example, controllers and processors in other components of a surgical system, such as for example the patient side cart and/or surgeon console, rather than as part of a separate auxiliary/control cart; control and processing architecture can also be distributed between various components of the surgical system as those having ordinary skill in the art would appreciate.

According to an exemplary embodiment, patient side cart 100 includes a base 102, a main column 104, and a main boom 106 connected to the main column 104. The patient side cart 100 also includes a plurality of teleoperated manipulator arms 110, 111, 112, 113 (sometimes referred to as patient side manipulators), which are each connected to the main boom 106, as depicted in the exemplary embodiment of FIG. 1. Manipulator arms 110, 111, 112, 113 may each include an instrument mount portion 120 to which an instrument 130 may be mounted, which is illustrated as being attached to manipulator arm 110. Portions of the manipulator arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124. A shaft 132 of instrument 130 extends through cannula mount 124 and mounted cannula, and on to a remote site during a surgical procedure. A force transmission mechanism 134 at a proximal end of instrument 130 is mechanically coupled with the actuation interface assembly 122, according to an exemplary embodiment. Persons skilled in the art are familiar with surgical instrument force transmission mechanisms, which receive a mechanical input force from a source (e.g., an electric motor on a manipulator arm supporting the instrument) and convert and/or redirect the received force to an output force to drive a component (e.g., a wrist, an end effector, etc.) at a relatively distal end portion of the instrument. Cannula mount 124 may be configured to hold a cannula 136 through which shaft 132 of instrument 130 may extend to a surgery site during a surgical procedure. Actuation interface assembly 122 may contain a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector such as forceps or graspers, a needle driver, a scalpel, scissors, a stapler, a cauterizing tool, etc., or may be an endoscopic imaging instrument or other sensing instrument used during a surgical procedure to provide information, (e.g., visualization, electrophysiological activity, pressure, fluid flow, and/or other sensed data) of a remote surgical site. In the exemplary embodiment of FIG. 1, a surgical instrument with an end effector or a sensing instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
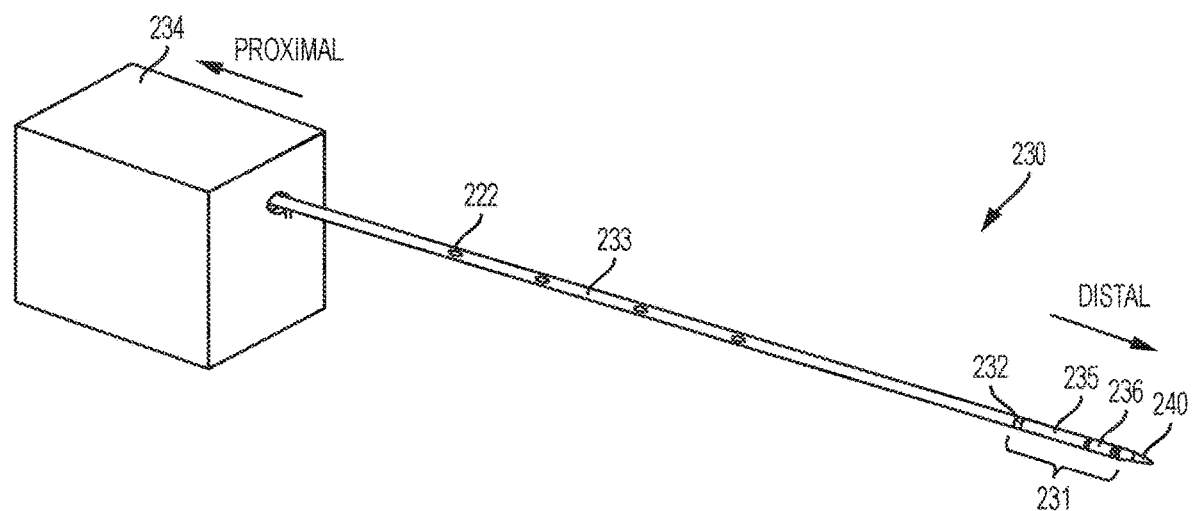
FIG. 2 is a perspective, diagrammatic view of a surgical instrument for use with the teleoperated surgical system of FIG. 1, according to an exemplary embodiment.

FIG. 2 shows an exemplary embodiment of a surgical instrument 230 in more detail. The surgical instrument 230 includes a shaft 233, a force transmission housing 234 disposed at a proximal end of the shaft 233, and an end effector 240 disposed at a distal end of the shaft 233. The exemplary embodiment of FIG. 2 further illustrates an embodiment of a surgical instrument having a wrist mechanism 231 and an end effector 240, which are the components of the instrument 230 that generally move extensively during a medical procedure. In the illustrated embodiment, the wrist mechanism 231 includes a joint 232 that connects an extended member 235 to the shaft 233, and extended member 235 connects to a multi-member wrist 236 on which effector 240 is mounted. Joint 232 can have two angular degrees of freedom for movement of member 235, which, as a result of the extended length of member 235, provides a significant range of spatial motion for the wrist 236 and the end effector 240. Wrist 236 includes multiple vertebrae that may be independently controlled to provide one or more degrees of freedom for moving and orienting end effector 240 during a medical procedure. The specifics of wrist mechanism 231 are provided here merely as an illustration of one type of wrist mechanism. Many other types of wrist mechanisms are known and could be used with removable sheaths as described herein. For example, U.S. Pat. No. 6,817,974, entitled "Surgical tool having Positively Positionable Tendon-Actuated Multi-Disk Wrist Joint," to Cooper et al. describes some known wrist mechanisms containing multiple disks and tendon controlled joints. In addition, those of ordinary skill in the art would appreciate that a surgical instrument can lack any wrist mechanism, with an end effector being couple directly to the shaft.

FIG. 2 also illustrates that shaft 233 may optionally include cleaning holes 222, which facilitate cleaning of the interior of the instrument 230 between medical procedures. In some cases, such cleaning holes have the drawback of creating flow paths for biological material or gas flow from a region of elevated pressure that may be maintained in a patient during a medical procedure. However, in accordance with exemplary embodiments of the disclosure, a replaceable sheath can be installed on instrument 230 and seal cleaning holes 222 to help prevent penetration of biological material or gas into the holes and to maintain a pressure differential during a medical procedure. Further, the sheath can be removed between medical procedures to permit access to cleaning holes 222 and other portions of the instrument when the instrument 230 is cleaned. Cleaning passages (not shown) also can be in wrist mechanism 231, for example as holes, in extended member 234 and/or via interstitial openings created by space between adjacent wrist structures and/or where an end effector is coupled to the shaft. The sheath can also seal wrist mechanism 231 but in case of contamination, can be removed to permit cleaning of an instrument protected by the sheath. On a camera instrument, which may be relatively large or have lower mechanical load requirements, the cleaning holes can be made large to enable easy cleaning, while the sheath reduces the amount of access that biomaterial has to the camera system during use. In some situations, instruments such as camera systems that are not generally in direct contact with biomaterial may not require a full seal.

Figure 3:
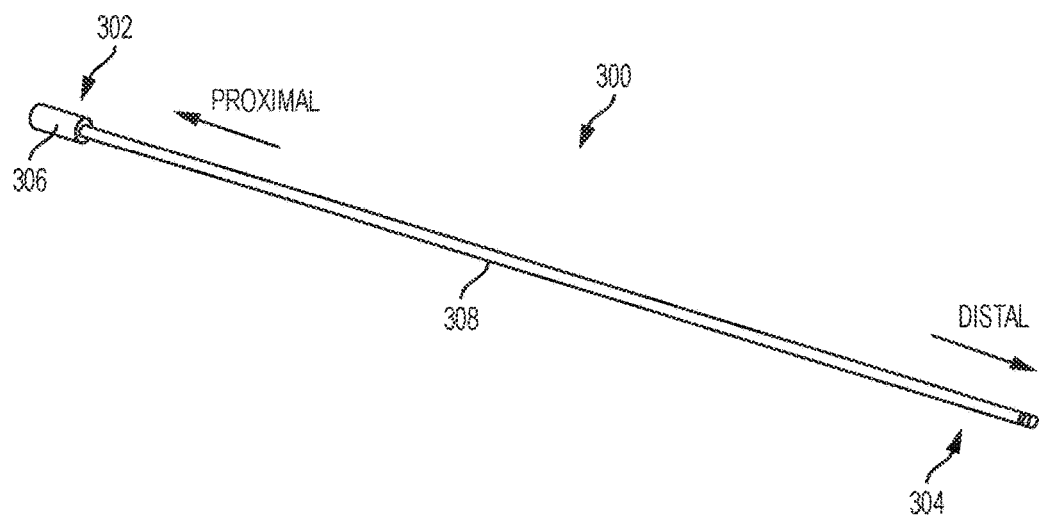
FIG. 3 is a perspective, diagrammatic view of a surgical instrument sheath according to an exemplary embodiment.

Referring now to FIG. 3, an exemplary embodiment of a protective sheath configured to cover at least a portion of the shaft of a surgical instrument, such as instrument 130 (FIG. 1) or instrument 230 (FIG. 2), is illustrated. As a non-limiting example, the sheath 300 of FIG. 3 may be similar in function, materials, and/or construction to the sheaths described at least in U.S. Pat. No. 9,089,351 to Park et al., issued Jul. 28, 2015, entitled "Sheath for Surgical Instrument," the disclosure of which is hereby incorporated by reference in its entirety. The sheath 300 has a proximal end 302, which in various exemplary embodiments may be disposed proximate a transmission housing when the protective sheath 300 is assembled on a surgical instrument, and a distal end 304, which may be disposed proximate the end effector and/or wrist mechanism of a surgical instrument when the protective sheath 300 is assembled on the instrument 130. Thus, in an exemplary embodiment, the sheath may extend to cover substantially the entire length of an instrument shaft from a proximal end transmission housing of the surgical instrument to an end effector or a sensing element, such as an imaging capture device, allowing enough exposure of the end effector or instrument such that it is able to perform its intended function.

Although the sheaths of various disclosed exemplary embodiment are configured to lockably engage with a sheath connector portion of a surgical instrument that is disposed where the instrument shaft meets the transmission housing, those having ordinary skill in the art will appreciate that connector portions can be provided at other locations along the surgical instrument, including at locations along the shaft distal to the transmission housing with appropriate modification.

The protective sheath 300 includes a retention mechanism 306 located at or near the proximal end 302. The retention mechanism 306 is configured to interact with (e.g., engage) one or more corresponding (e.g., complementary) features (not shown in FIG. 3) disposed on a portion of a surgical instrument to lockably engage and retain the sheath 300 in an assembled configuration on the instrument. While the retention mechanism 306 is illustrated in FIG. 3 as attached to a sleeve 308 of the sheath 300, the retention mechanism 306 may be or include one or more features formed in the sleeve 308 of the sheath 300, for example, as described in greater detail below in connection with the exemplary embodiment of FIGS. 10A and 10B.

The sheath sleeve in accordance with various exemplary embodiments herein may be made of various relatively flexible and biocompatible materials that are selected to impart various properties as desired, including, dielectric materials, porous materials that allow gases to permeate the sheath sleeve wall while preventing passage of biomaterials and liquid, relatively durable to protect against damage due to other surgical instruments and structures rubbing against the sheath, etc. While the sheath sleeve can be made of a single material, the present disclosure also contemplates sheath sleeves made of different materials, such as differing layers of materials and/or materials having differing properties along different length portions of the sleeve. In exemplary embodiments, the various sheath tube/body structures and materials used to make such structures disclosed U.S.

Pat. No. 9,089,351 B2, issued Jul. 28, 2015 (entitled "SHEATH FOR SURGICAL INSTRUMENT"), incorporated by reference herein, can be used to make the sheath sleeves of the present disclosure.

In some exemplary embodiments, such as those shown and described in connection with FIGS. 4A through 9D, a sheath retention mechanism includes one or more resilient portions configured to provide a lockable engagement with a complementary feature of the surgical instrument. The resilient portions may comprise resilient deflection portions configured to deflect as they move past the complementary feature of the instrument as the sheath is fitted over the instrument, and to engage the complementary feature of the surgical instrument once the sheath 300 is assembled with the instrument.

Application of sufficient force to one or more force application surfaces of the retention mechanism causes the resilient portions to deflect so as to disengage the retention mechanism from the complementary feature of the instrument, thereby enabling removal of the sheath from the instrument.

Figure 4A:
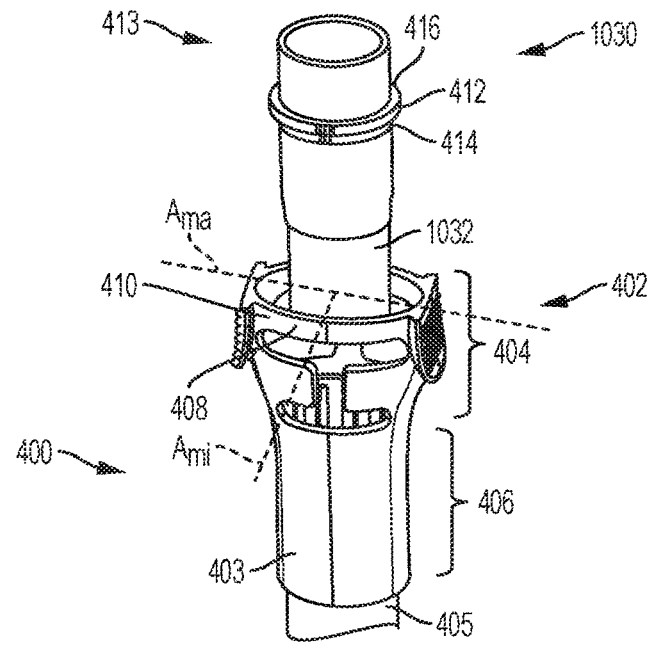
FIG. 4A is a perspective view of a sheath retainer body and a sheath connector portion of a surgical instrument in an unassembled configuration, according to an exemplary embodiment.

FIG. 4A shows an exemplary embodiment of a sheath 400 including a retention mechanism 402 configured to interact with a sheath connector portion 413 of a surgical instrument 1030, which may have a configuration similar to surgical instrument 230 in FIG. 2, with the connector portion being provided at the juncture between the instrument shaft and a transmission housing (e.g., housing 234 in FIG. 2) in an exemplary embodiment. In the embodiment of FIG. 4A, the retention mechanism 402 comprises a generally tubular-shaped retainer body 403 affixed to a proximal end portion of a sheath sleeve 405. The retainer body 403 has a sheath sleeve attachment portion 406 disposed at a distal end portion of the body 403. The sheath sleeve attachment portion 406 is configured to be affixed to the sleeve 405 of the sheath 400, as will be described in further detail below. Extending proximally from the sheath sleeve attachment portion 406 is a locking collar 404 that defines a proximal end 408 of the retainer body 403. The locking collar 404 comprises one or more resilient members 410. The resilient members 410 may be integrally formed (e.g., molded) with the retainer body 403, as shown in FIG. 4A, or may comprise components of the retention mechanism 402 formed separately from the retainer body 403.

The resilient members 410 are configured to lockably engage one or more complementary retention features 412 of the sheath connector portion 413 of the instrument 1030 when the sheath 400 is in an assembled configuration on the instrument. In the depicted exemplary embodiment, the complementary retention feature 412 of the sheath connector portion 413 includes a circumferentially disposed protrusion with a ramped portion 414, which may have a generally frustoconical surface profile with an acute angle relative to a longitudinal axis of the instrument shaft 1032. More specifically, the ramped portion 414 extends upwardly and outwardly in a direction from distal to proximal along an axial direction of the surgical instrument. In this way, as the surfaces of the resilient members 410 come into contact with the beginning of the ramped portion 414 they are gradually spread apart by the ramped portion 414 as a continued force is exerted on the retainer body 403 sliding it over the connector portion 413. Eventually, the resilient members 410 move proximally past the complementary retention feature 412 and spring back to their initial, undeformed configuration. A retaining surface 416 of the retention feature 412, is disposed substantially orthogonal to the longitudinal axis of the shaft 1032 and provides a shoulder that prevents axial downward movement of the sheath in an assembled configuration of the sheath on the instrument by interaction with the resilient members 410. In other words, in their undeformed configuration, the resilient members come into contact with the shoulder provided by the surface 416 to prevent the axial movement in a distal direction of the retention mechanism 402, and thus the sheath.

Those having ordinary skill in the art would appreciate that the retention feature 412 may be a continuous feature around the circumference of the connector portion 413, or may be plural features disposed in select locations around the circumference, which may assist in orienting the sheath in a desired rotational positioning relative to the instrument.

The sheath 400 may be placed in the assembled configuration on the instrument 1030 by advancing the locking collar 404 of the retainer body 403 over the sheath connector portion 413 of the instrument 1030. As the locking collar 404 is moved axially into engagement with the sheath connector portion 413 of the surgical instrument (i.e., moving the locking collar 404 in a proximal direction), the ramped portion 414 of the retention feature 412 come into contact with resilient members 410. Continued movement of the locking collar 404 proximally cause the resilient members 410 to be deflected laterally (e.g., radially) outwardly by the ramped portion 414. The deflection of the resilient members 410 radially outwardly allows the complementary retention feature 412 to pass between and move axially past the resilient members 410.

Figure 4B:
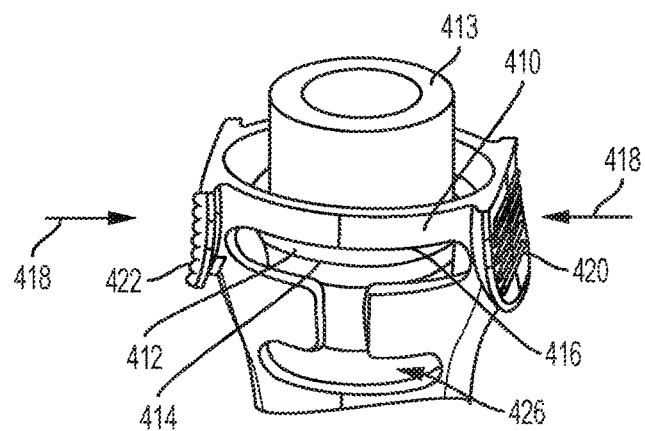
FIG. 4B is a perspective view of the sheath retainer body and sheath connector portion of FIG. 4A in an assembled configuration.

As shown in FIG. 4B, once the resilient members 410 have cleared the ramped portion 414 of the complementary retention feature 412, the resilient members 410 return to their initial, undeflected configuration and are positioned proximal to the retaining surface 416 of the complementary retention feature 412. Relatively rapid movement of the resilient members 410 as they return to their undeflected configuration and contact a portion of the sheath connector portion 413 of the instrument 1030 may create an audible or tactile indication that the sheath 400 has fully engaged the sheath connector portion 413 of the instrument 1030. For example, such an indication may include one or more of an audible noise (e.g., a "click"), a low-frequency vibratory wave traveling through the retention feature 412 that results in a tactile sensation in an operator, or the like. Due to the shoulder of the retaining surface 416, a mechanical interference between the retaining surface 416 (FIG. 4A) of the complementary retention feature 412 and the one or more resilient members 410 retains (locks) the sheath 400 in position over the shaft 1032 of the instrument 1030, preventing axial movement and disassembly of the retaining mechanism 402 relative to the surgical instrument absent a sufficient force acting on the instrument or sheath retention mechanism 402.

Following use of the instrument 1030 and sheath 400, (e.g., in a surgical procedure), it may be necessary or desirable to remove the sheath 400 to clean (e.g., sterilize) the instrument 1030, for example reprocessing it for reuse. Referring still to FIG. 4B, to remove the sheath 400 from the instrument 1030, a force 418 directed radially inwardly (e.g., a squeezing force) may be applied to the proximal end 408 of the retainer body 403, for example, at locations on the proximal end 408 substantially ninety degrees apart from the resilient members 410. For example, the retainer body 403 may be grasped (e.g., pinched) by an operator at force application surfaces 420, 422. Radially inwardly directed force applied to the force application surfaces 420, 422 may cause portions of the proximal end 408 of the retainer body 403 located at and around the force application surfaces 420, 422 to deflect inward toward the sheath connector portion 413 of the instrument 130, while the resilient members 410 deflect away from sheath connector portion 413. In other words, the lateral (e.g., radial) distance the resilient members 410 may increase as the compressive force 418 is applied to the force application surfaces 420, 422. The outward deflection of the resilient members 410 laterally (e.g., radially) beyond retention feature 412 allows the resilient members 410 to clear the complementary retention feature 412, enabling the locking collar 404 to be disengaged (unlocked) from the connector portion 413 and the sheath 400 removed from the instrument 1030 by moving the retention mechanism 402 and sheath sleeve distally relative to the instrument 1030.

In some exemplary embodiments, the resilient members 410 and/or other portions of the retainer body 403 elastically deform under the force 418. Additionally or alternatively, the resilient members 410 and/or the other portions of the retainer body 403 may plastically deform under the force 418. In some embodiments, the sheath 400 may be disposed of after a single use.

The retainer body 403 of the sheath 400 may be made from a resilient material to facilitate deflection of the resilient members 410 and the force application surfaces 420, 422. As non-limiting examples, the retainer body 403 is made from a thermoplastic such as nylon, polyether block amide (PEBAX), high-density polyethylene (HDPE), or other polymers. In some embodiments, the retainer body 403 is made of a composite material, such as a fiber-reinforced polymer, and/or may include non-polymer materials. The retainer body 403 may be made using forming processes such as injection molding, casting, negative manufacturing processes such as machining, and/or additive manufacturing processes such as fused deposition modeling, powder bed sintering, etc. In some embodiments, the retainer body 403 and the sheath sleeve 405 are made of the same or similar materials so as to facilitate attachment of the retainer body 403 to the sheath sleeve 405. In one exemplary embodiment, the retainer body 403 and the sheath sleeve 405 both comprise polyether block amide. However, the retainer body 403 and other portions or components of the sheath 400 may include any materials that exhibit suitable characteristics. For example, in some embodiments, a material may be chosen at least in part based on stiffness, elastic modulus, or other mechanical characteristics that may be desired. As a non-limiting example, some suitable materials may exhibit an elastic modulus ranging from about 500 MPa to about 5000 MPa. Other suitable materials may include elastic moduli of less than about 500 MPa or greater than about 5000 MPa, for example, while wall thicknesses are adjusted to compensate. In some embodiments, a material also may be chosen based on manufacturing characteristics, such as moldability, machinability, etc. Materials also may be chosen based at least in part on the cost of raw materials, the costs associated with manufacturing processes suitable in working with such materials, etc. In some embodiments, a relatively low-cost material may be desirable, e.g., for a sheath limited to a single use (i.e., disposable). Other material selection criteria may include, without limitation, the ability of the material to withstand various sterilization processes without significant degradation (e.g., gamma sterilization, ethylene oxide sterilization, autoclave, e-beam sterilization, etc.); and the biocompatibility of the material, such as, for example, being latex free.

The retainer body 403 and the sheath sleeve 405 may be attached to one another by any suitable method. As a non-limiting example, the retainer body 403 and the sheath sleeve 405 may be fused to one another by a welding process such as ultrasonic welding, laser welding, spin fusing, etc. In some exemplary embodiments, an adhesive may be used to affix the retainer body 403 to the sheath sleeve 405. In one exemplary embodiment, the retainer body 403 is affixed to the sheath sleeve 405 using one or more spot welds. In some embodiments, the sheath sleeve 405 may be attached to the retainer body 403 with a mechanical attachment device, as described in greater detail below in connection with FIGS. 8A through 8C.

The retainer body 403 may have a geometry configured to facilitate deformation of the resilient members 410 for installation and removal of the sheath 400. For example, in the embodiment of FIGS. 4A and 4B, the retainer body 403 may have a cross-sectional shape that gradually transitions from a circular interior transverse cross-section along the sheath sleeve attachment portion 406 to an elongated (e.g., oval or elliptical) interior transverse cross-section at the proximal end 408 and locking collar 404. In an initial, undeformed state, the force application surfaces 420, 422 may be oriented at opposite ends of a major axis $A_{ma}$ of the oval, while portions of the resilient members 410 are positioned at opposite ends of a minor axis $A_{mi}$ of the oval. When force is applied to the force application surfaces 420, 422, the major axis $A_{ma}$ shortens while the minor axis $A_{mi}$ lengthens, and the elongated cross-sectional shape of the proximal end 408 and locking collar, at least around the resilient members 410, deforms. In some embodiments, under deformation due to a force applied to the force application surfaces 420, 422, the major and minor axis $A_{ma}$, $A_{mi}$ may become substantially equal and the cross-sectional shape of the retainer body 403 at the proximal end 408, including at least the resilient members 410 and proximate the force application surfaces 420, 422, becomes substantially circular. Elongation of the minor axis $A_{mi}$ by a sufficient amount results in the resilient members 410 deflecting radially outwardly by an amount sufficient to permit disengaging (unlocking) from the complementary retention feature 412 of the instrument 1030.

The retainer body 403 may be configured such that the compressive force 418 required to be applied to the force application surfaces 420, 422 to deform the resilient members 410 sufficiently to remove the sheath 400 is below a certain threshold. For example, the retainer body 403 may be configured such that the force 418 required to be applied to the force application surfaces 420, 422 to remove the sheath 400 is low enough that an operator (e.g., physician, nurse, etc.) can remove the sheath 400 by applying force 418 manually, for example, with one hand. As a non-limiting example, the compressive force 418 required to be applied to the force application surfaces 420, 422 may range from about 2 pound-force ($lb_f$) to about 10 pound-force ($lb_f$), for example about 4 pound-force ($lb_f$). However, the applied force required may be higher, for example, if tools designed to apply the force are used instead of the force being applied by a user's hand.

The magnitude of the compressive force 418 required to be applied to the force application surfaces 420, 422 may depend at least partially on the properties of the materials from which the retainer body 403 is constructed. For example, a material with a relatively higher modulus of elasticity may require a correspondingly higher force compared to a material with a relatively lower modulus of elasticity. Additionally, the geometry of the retainer body 403 may affect the magnitude of the force 418 required to remove the sheath 400 from the instrument 1030. For example, relatively thicker walls of retainer body 403 and relatively thicker resilient members 410 may require a relatively greater force to remove the sheath 400 than relatively thinner components.

The force application surfaces 420, 422 may include features configured to facilitate manipulation by the operator. For example, the force application surfaces 420, 422 may include features such as ridges 424, knurling, or other textures or features, to improve grip and/or to enable tactile recognition of force application surfaces 420, 422.

Additionally, the retainer body 403 may include reliefs configured to alter the magnitude of the compressive force 418 that results in deflecting the resilient members 410 to remove the sheath 400. The reliefs may increase flexibility (e.g., elastic deformability) of the locking collar 404 so as to concentrate stress in the resilient members 410, resulting in greater deflection of the resilient members 410 for a given applied force. Furthermore, the reliefs may relieve areas of the locking collar 404 that may otherwise experience relatively high stress, which may cause plastic deformation, fractures, etc. in the locking collar 404. While the reliefs 426 shown in FIGS. 4A and 4B are configured as an "I" shape cut-out portion, configurations different from that shown are contemplated. Aside from providing a cut-out portion of the wall of the locking collar, reliefs may be provided by other weakening of the retainer body wall, such as by using a different and/or thinner material at certain locations around the circumference of the body 403. Additionally, some embodiments may not include any reliefs. Such embodiments may include one or more radially inwardly extending protrusions or shoulders located at the proximal end 408 of the retainer body 403 configured to interact with the complementary retention feature 412 in substantially the same manner as the resilient members 410 described above. For example, the retainer body 403 may include an undercut on an internal surface, a portion of which forms a distal-facing surface that interacts with a proximally-facing surface of the complementary retention feature 412.

Various exemplary embodiments also contemplate preventing rotation of a sheath relative to the instrument once the sheath is in an assembled configuration on the instrument. For example, rotation of the sheath with respect to the instrument shaft during use or transportation may cause the sheath 400 to rip, tear, or otherwise degrade. However, for ease and speed of installation, it may be undesirable to require the operator to align the sheath in a particular rotational alignment with respect to the instrument.

Figure 5:
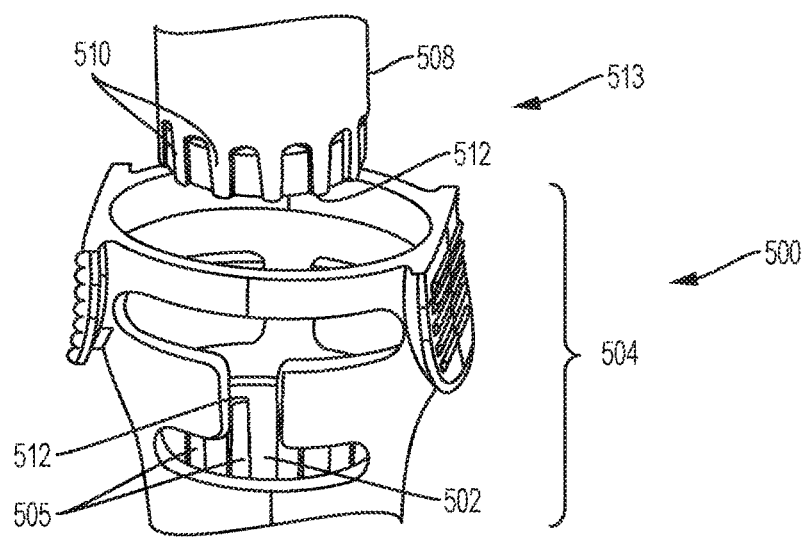
FIG. 5 is a perspective view of a sheath retainer body and a sheath connector portion of a surgical instrument according to another exemplary embodiment.

Accordingly, FIG. 5 shows another embodiment of a retention mechanism 500 according to an exemplary embodiment of the present disclosure. Functionality of the retention mechanism 500 may be similar in many respects to the functionality of the retention mechanism 402 described in connection with FIGS. 4A and 4B. For clarity, shaft 1032 (FIG. 4A) of instrument 1030 (FIG. 4A) is omitted from the illustration in FIG. 5. The sheath retention mechanism 500 has an internal surface 502 of a distal portion of the locking collar 504 that includes a plurality of longitudinally oriented and circumferentially spaced internal splines 505. A sheath connector portion 513 of an instrument (not shown) may have an outer surface 508 with a plurality of longitudinally oriented and circumferentially spaced recesses 510 configured to interface with the internal splines 505. When the sheath retention mechanism 500 is engaged with the sheath connector portion 513 of the instrument, the internal splines 505 are received in the recesses 510 to align and prevent rotation of the sheath retention mechanism 500 relative to the sheath connector portion 513, and thus prevent rotation of the sheath relative to the instrument in the assembled, locked configuration of the retention mechanism 500 on the connector portion 513.

In some embodiments, the internal splines 505 and the recesses 510 may include features and/or geometry configured to facilitate self-aligning of the sheath retention mechanism 500 with the sheath connector portion 506. For example, the internal splines 505 and/or the edges of the connector portion between recesses 510 can have a rounded leading ends 512. As the sheath retention mechanism 500 is slid into engagement with the sheath connector portion 513, the rounded leading ends 512 facilitate self-aligning of the internal splines 505 and the recesses 510. Thus, the sheath retention mechanism 500 is configured to self-align with the sheath connector portion 513 with minimal or no external rotational forces by a user. The number of rotational orientations at which the sheath retention mechanism 500 can be installed on the sheath connector portion 513 of the instrument 1030 may be determined at least in part by the number and/or configuration of the internal splines 505 and the recesses 510. For example, the pitch of the internal splines 505 and the recesses 510 may determine the number of rotational orientations in which the sheath retention mechanism 500 can be installed on the sheath connector portion, a greater pitch resulting in more possible installed rotational orientations, and a lesser pitch resulting in fewer possible installed rotational orientations.

Additionally, in some embodiments, the sheath retention mechanism 500 and the sheath connector portion 513 may include features configured to require alignment of the sheath retention mechanism 500 with the sheath connector portion 513 in one or more predetermined rotational orientations. For example, one or more of the internal splines and a corresponding one or more of the recesses may have a different size, shape, and/or configuration than the remaining internal splines and recesses, such that the one or more internal splines and the corresponding one or more recesses having the different size, shape, and/or configuration must be rotationally aligned with one another before the sheath retention mechanism 500 can be fully installed on the sheath connector portion 513.

Figure 6:
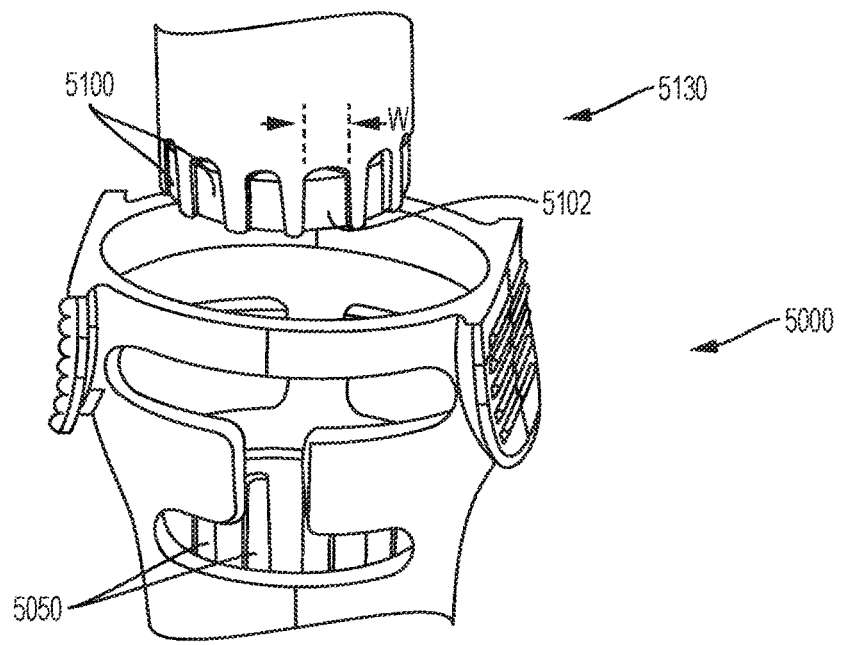
FIG. 6 is a perspective view of a sheath retainer body and a sheath connector portion of a surgical instrument according to yet another exemplary embodiment.

For example, as shown in FIG. 6, a sheath retention mechanism 5000 includes a plurality of internal splines 5050, and a sheath connector portion 5130 includes a plurality of recesses 5100. At least one recess 5102 of the plurality of recesses 5100 has a different dimension (e.g., a different circumferential width W around the sheath connector portion 5130) than other recesses of the plurality of recesses 5100, and a corresponding at least one spline (not shown) of the plurality of internal splines 5050 has a circumferential width corresponding to the circumferential width w of the at least one recess 5102. Thus, the at least one recess 5102 must be aligned with the corresponding at least one spline (not shown) before the sheath retention mechanism 5000 can be fully installed on the sheath connector portion 5130. While the embodiment of FIG. 6 shows the at least one recess 5102 having a greater width w than other recesses of the plurality of recesses 5100, additional or other dimensions or features of the at least one recess 5102 may be altered with respect to the other recesses of the plurality of recesses 5100. For example, one or more of a length, a depth (e.g., radial dimension) or a shape of the at least one recess 5102 and the corresponding at least one spline may be altered with respect to the other recesses of the plurality of recesses 5100 and splines of the plurality of internal splines 5050.

Some embodiments may include multiple splines and corresponding recesses having different dimensions than the other splines and recesses, which may be spaced around the circumference of the sheath retention mechanism 5000 and the sheath connector portion 5130 to provide multiple possible installation orientations. For example, two splines and corresponding recesses having a different dimension than the other splines and recesses may be spaced 180 degrees apart around the circumference of the sheath retention mechanism 5000 and the sheath connector portion 5130 to provide two possible installation orientations, 180 degrees apart. Three splines and corresponding recesses having a different dimension than the other splines and recesses may be spaced 120 degrees apart to provide three installation orientations 120 degrees apart, four splines and corresponding recesses having a different dimension than the other splines and recesses may be spaced 90 degrees apart to provide four installation orientations 90 degrees apart, etc. Constraining the rotational orientation of the sheath retention mechanism 5000 with respect to the sheath connector portion 5130 may enable design and/or material properties of the sheath to be tailored for a particular movement or range of movements of an instrument shaft and/or end effector of a surgical instrument to which the sheath is attached. Those having ordinary skill in the art would appreciate that various other configurations, arrangements, and numbers of splines and recesses may be used to achieve a desired engagement and/or rotational alignment.

Figure 7A:
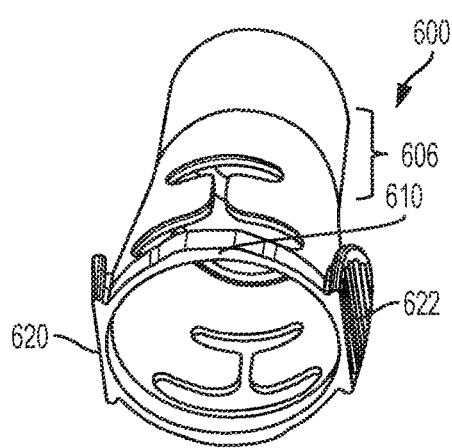
FIG. 7A is a top and side perspective view of a sheath retainer body according to another exemplary embodiment.
Figure 7B:
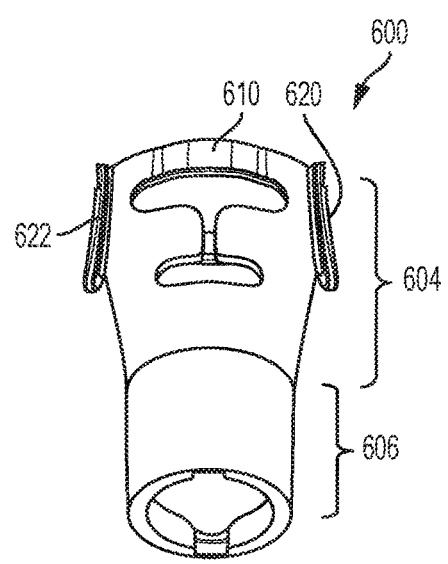
FIG. 7B is a bottom and side perspective view of a sheath retainer body according to the embodiment of FIG. 7A.

FIGS. 7A and 7B show yet another exemplary embodiment of a sheath retention mechanism according to the present disclosure. The sheath retention mechanism 600 may be configured similarly to the exemplary embodiment of FIGS. 4-5, with differences being described below. In this embodiment, the sheath retention mechanism 600 includes a sheath sleeve attachment portion 606 with a substantially elongated (e.g., oval or elliptical) interior transverse cross-sectional shape, as shown in FIG. 7A, so as to be configured to receive a similarly shaped sheath sleeve of elongated cross-section (e.g., oval or elliptical) (not shown)) configured to cover an instrument shaft having an elongated (e.g., oval or elliptical) outer transverse cross-sectional shape, such as instrument shaft 632 partially depicted in FIG. 7C. The cross-sectional shape of the sheath retention mechanism 600 may gradually transition from the oval shape of sheath sleeve attachment portion 603 to a substantially circular interior transverse cross-sectional shape at the locking collar 604 including the proximal end, as shown in FIG. 7A. As in the embodiments of FIGS. 4 and 5, oppositely disposed resilient members 610 and oppositely disposed force application surfaces 620, 622 are provided at the proximal end of the locking collar 604, with the resilient members 610 being offset ninety degrees from the respective force application surfaces 620, 622.

Figure 7C:
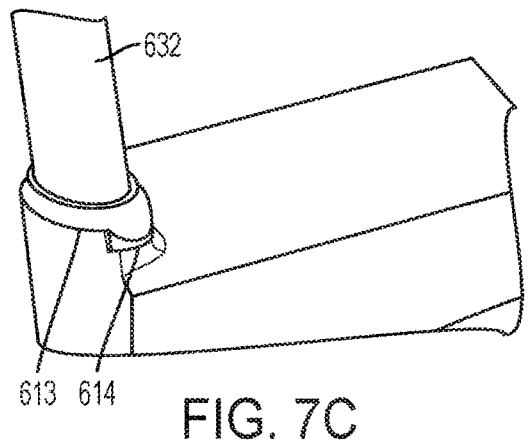
FIG. 7C is a detailed, partial perspective view of a surgical instrument according to another exemplary embodiment.

With reference now to FIG. 7C, the sheath retention mechanism 600 and associated sheath sleeve (not shown) may be installed on an instrument with a sheath connector portion 613 and instrument shaft 632. The sheath connector portion 613 may have a shape corresponding to the shape of the cross-section and opening of the sheath sleeve attachment portion 606 of the sheath retention mechanism 600, such as, for example, oval or elliptical. The sheath connector portion 613 may include a complementary retention feature such as plurality of protrusions 614. For example, as shown in FIG. 7C, the sheath connector portion 613 may include two protrusions 614 located at opposite ends of a major axis of the oval shape of the connector portion 613. The sheath may be installed on the instrument by guiding the sheath retention mechanism 600 and sleeve over the distal end of the instrument (not shown) and advancing the sheath retention mechanism 600 and sheath sleeve along the instrument shaft 632 and over the sheath connector portion 613. As the locking collar 604 of the sheath retention mechanism 600 contacts the elliptical (or oval-shaped) sheath connector portion 612, the gradual transition between the circular cross section of the opening of the locking collar 604 and the oval cross section of sheath sleeve attachment portion 606 orients the retention mechanism 600 into alignment with the elliptical (or oval-shaped) sheath connector portion 612 and shaft 632 of the surgical instrument in one of two orientations (e.g., such that the major axes of the sheath attachment portion 606 is aligned with the major axis of the sheath connector portion 613 and shaft 632 in a first orientation, or in a second orientation rotated 180 degrees from the first orientation).

Figure 7D:
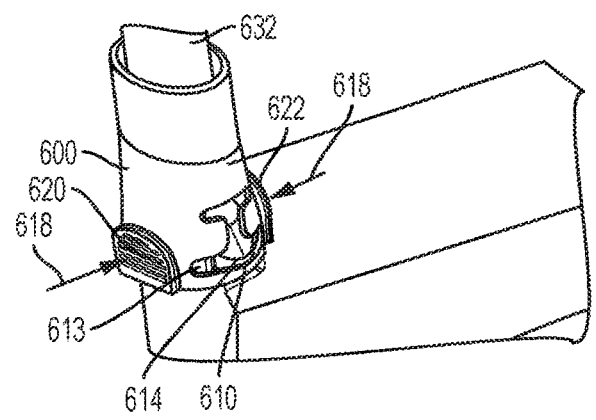
FIG. 7D is a perspective view of the sheath retainer body of FIGS. 7A and 7B in an assembled configuration on the surgical instrument of FIG. 7C.

In a manner similar to the exemplary embodiments of FIGS. 3-5 discussed above, with the continued advancement of the sheath proximally relative to the instrument, the resilient members 610 of the sheath retention mechanism 600 deflect laterally (e.g., radially) outward as they come into contact the distally positioned ramped surface of the protrusions 614 of the sheath connector portion 612, allowing them to provide sufficient clearance to move proximally past the protrusions 614. Due to their resiliency, once they are past the protrusions 614, the resilient members 610 return to their initial position (i.e., return to an undeformed configuration), as shown in FIG. 7D. In the assembled configuration of the retention mechanism 600 over the sheath connector portion 613 shown in FIG. 7D, the interference between the protrusion 614 and the resilient members 610 prevent the retention mechanism 600 and sheath from moving axially relative to the instrument and thus locks the sheath in position on the instrument shaft 632. The protrusions 614 can have a surface similar to that described above with respect to the retention features of the exemplary embodiments of FIGS. 3-5 to provide an interference of the resilient members 610 and the protrusions 614, thereby preventing the retention mechanism 600 and sheath sleeve attached thereto from being removed axially relative to the instrument.

To remove the sheath retention mechanism 600 and sheath from the instrument, a laterally (e.g., radially) inwardly directed force 618 is applied to the force application surfaces 620, 622, causing the locking collar 604, at least at the proximal end portion including the resilient members 610 of the sheath retention mechanism 600, to deform from its circular cross-sectional shape into an elongated (e.g., oval or elliptical) cross-sectional shape, thereby increasing the distance between the resilient members 610. Under sufficient applied force 618, the distance between the resilient members 610 increases so as to disengage (unlock) from the protrusions 614, and provide sufficient clearance to move the retention mechanism 600 distally past the protrusions 614. The sheath retention mechanism 600 can then be disengaged from the sheath connector portion 613 and the sheath removed from the instrument.

In yet another exemplary embodiment, a sheath retention mechanism may be configured to provide a mechanical attachment to the sheath sleeve, as opposed to a thermal fusing or adhesive bond. In some instances, the sleeve of a sheath may be difficult or impossible to fuse or bond to the retention mechanism of the sheath, due to material properties of the sheath sleeve, the retention mechanism, or both. For example, in some embodiments, the sheath sleeve may be made of a material, such as polytetrafluoroethylene (PTFE), which may not readily weld or otherwise bond to other materials from which the retention mechanism is likely to be made. Accordingly, the sheath sleeve of the sheath and the retention mechanism may be attached together using mechanical attachment components, as described below.

Figure 8A:
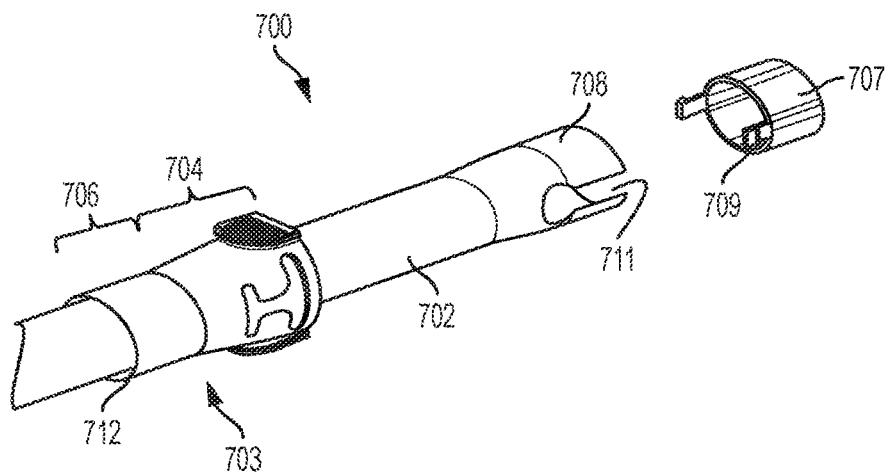
FIG. 8A is a perspective view a sheath and sheath retainer body in an unassembled configuration according to another exemplary embodiment.
Figure 8B:
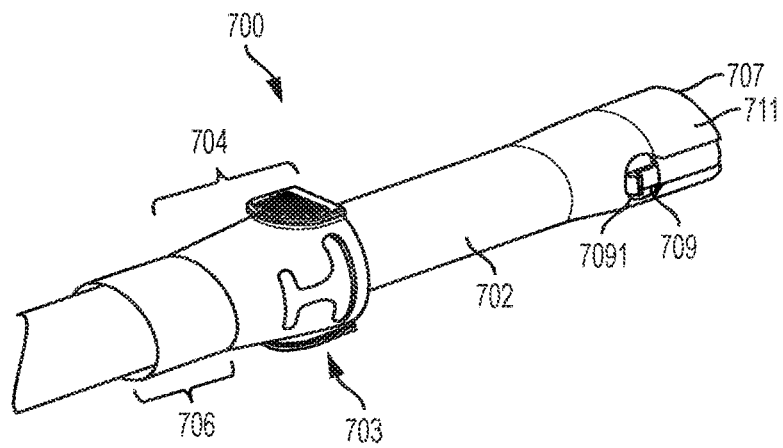
FIG. 8B is a perspective view of the sheath and retainer body according to the embodiment of FIG. 8A in a partially assembled configuration.
Figure 8C:
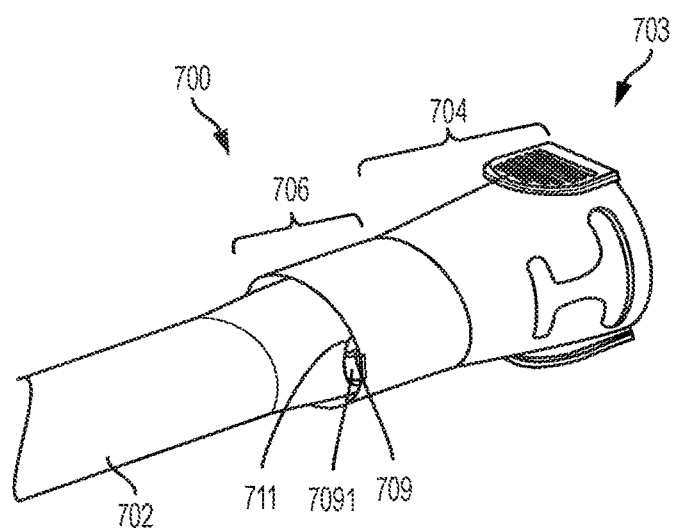
FIG. 8C is a perspective view of the sheath and retainer body of FIGS. 8A and 8B in a fully assembled configuration.

With reference now to the exemplary embodiment of FIG. 8A, a sheath 700 includes a sheath sleeve 702 and a retention mechanism that has an outer retention mechanism part 703 and an inner retention mechanism part 707. The outer retention mechanism part 703 can be configured similar to the retention mechanism embodiments of FIGS. 3-6, with the exception of including an engagement feature for attachment to the inner retention mechanism part 707, as described below. For example, the outer retention mechanism part 703 is configured to receive a proximal portion of a sheath sleeve 702, and has a sheath sleeve attachment portion 706 and a locking collar 704 that extends from the sheath sleeve attachment portion 706. The inner retention mechanism part 707 is configured to be inserted within the proximal end portion 708 of the sheath sleeve 702, as shown in FIGS. 8B and 8C. The outer retention mechanism part 703 and the inner retention mechanism part 707 include interlocking features configured to mechanically couple the inner retention mechanism part 707 to the outer retention mechanism part 703, capturing the proximal end portion 708 of the sheath sleeve 702 therebetween. For example, the inner retention mechanism part 707 may include deflectable retaining tabs 709 configured to engage with the distal end 712 of the sheath sleeve attachment portion 706 of the outer retention mechanism part 703.

Referring now to FIG. 8C, the outer retention mechanism part 703 can be positioned over the proximal end portion 708 of the sheath sleeve 702 and over the inner retention mechanism part 707 positioned within the proximal end portion 708 of the sleeve 702 (FIG. 8B). As can be seen in FIG. 8A, the proximal end portion 708 includes longitudinally oriented cutout portions 711 in a side wall of the sleeve, positioned and configured to receive the deflection tabs 710 of the inner retention mechanism part 707. In the exemplary embodiment of FIGS. 8A-8C, there are two deflectable retaining tabs 709 disposed opposite each other around the inner retention mechanism part 707 and two cutout portions 711 disposed opposite each other around the proximal end portion 708 of the sleeve 702. However, those of ordinary skill in the art would appreciate that the present disclosure is not limited to the use of two deflectable retaining tabs and any number including one or more than two could be used.

The retaining tabs 709 on the inner retention mechanism part 707 deflect inwardly as the sleeve attachment portion 706 of the outer retention mechanism part 703 is brought over the proximal end portion 708 of the sleeve 702 and into engagement with radially outwardly extending protrusions 7091 on the end of the tabs 709. When the outer retention mechanism part 703 reaches its final position, shown in FIG. 8C, the distal end 712 of the sleeve attachment portion 706 comes to rest just above the end of the cutout portions 711, allowing radially outwardly extending protrusions 7091 to be released from contact with the inner surface of the sleeve attachment portion 706, thereby returning the deflectable retaining tabs 709 to their initial configuration with protrusions 7091 extending through the cutout portions 711 and providing a surface to prevent distal axial movement of the outer retention mechanism part 703 (see FIG. 8C). Mechanical interaction (e.g., a clamping force) acting on the sheath sleeve 702 by the inner retention mechanism part 707 and the outer retention mechanism part 703 thus secures the sleeve 702 to the retention mechanism.

Figure 9A:
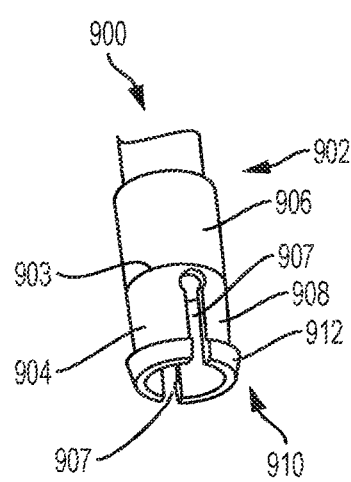
FIG. 9A is a perspective view of a sheath on an instrument shaft according to yet another exemplary embodiment.

Another exemplary embodiment of a sheath and instrument sheath connector portion is shown in FIGS. 9A through 9D. As shown in FIG. 9A, the sheath 900 has a proximal end portion 902 with a retention mechanism 903 secured thereto. The retention mechanism includes a sheath sleeve attachment portion 906 and a locking collar 904 having longitudinally extending reliefs 907, such as cut-outs or regions of weakened or thinner material extending generally axially so as to separate the locking collar 904 into deflectable segments 910. At the free end of the locking collar, the deflectable segments 910 terminate in an annular, outwardly extending protrusions (which can be in the shape of barbs) 912 with a ramped leading end, the surface of which tapers inwardly in a proximal to distal direction of the sheath.

Figure 9B:
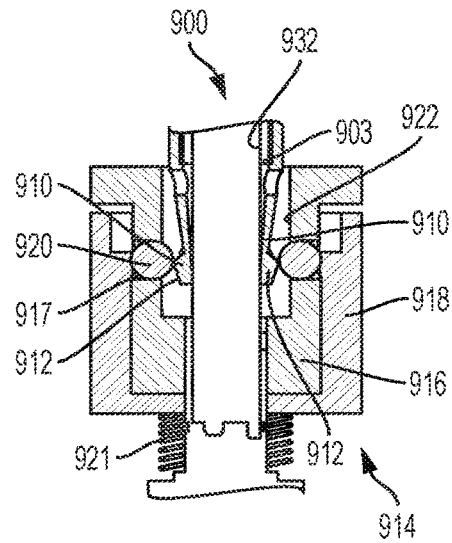
FIG. 9B is a cross-sectional view of the sheath of FIG. 9A and a sheath connection device of a surgical instrument according to an exemplary embodiment.
Figure 9C:
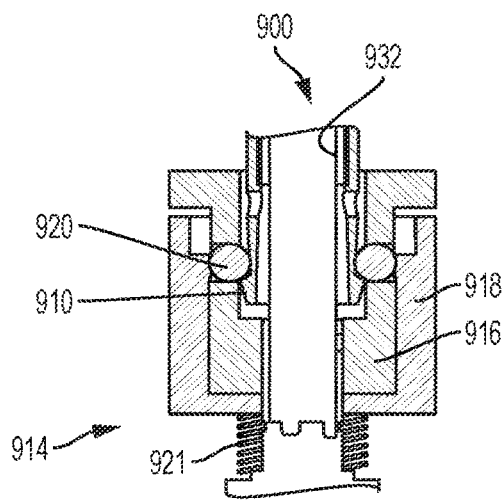
FIG. 9C is a cross-sectional view of the sheath and sheath connection device according to the embodiment of FIGS. 9A and 9B.

Referring now to FIG. 9B, the sheath 900 may be placed in an assembled configuration with a sheath connector portion 914 of an instrument. The sheath connector portion 914 includes an inner collar 916 and an outer collar 918 biased to a distal position (e.g., the position shown in FIG. 9B) by a biasing element (e.g., a coil spring) 921. Spherical biased retainer members 920 (e.g., ball bearings) are trapped within through holes 917 that extend through a lateral sidewall of the inner collar 916 as a result of an inner surface of the outer collar 918 closing the outer surface openings of the through holes when the outer collar 918 is in the locking position depicted in FIG. 9C. With reference to FIG. 9B, as the sheath retention mechanism 903 is inserted into the inner collar 916, the segments 908 of the locking collar 904 deflect radially inward as the leading ends of the protrusions 912 bear against the retainer members 920. As shown in FIG. 9C, once the protrusions 912 move proximally past the retainer members 920, the segments 908 return to the initial, undeflected position. As shown in FIG. 9C, in the assembled (locked) configuration of the sheath on the instrument shaft 932, the distal facing surface of the protrusions 912 forms a shoulder that engage with the retainer members 920 to prevent the sheath 900 from being moved distally and removed from the sheath connector device 914.

Figure 9D:
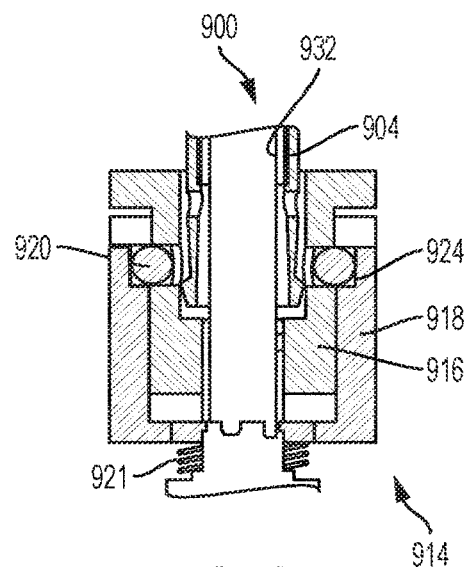
FIG. 9D is a cross-sectional view of the sheath and sheath connection device according to the embodiment of FIGS. 9A through 9C.

Now referring to FIG. 9D, the sheath 900 may be unlocked and removed from the sheath connector device 914, and thus the instrument shaft 932, by moving the outer collar 918 axially and proximally with respect to the inner collar 916 and against a biasing force of the biasing element 921 until an annular relief 924 on an inner surface of the outer collar 918 aligns with the retaining members 920. The retaining members 920 may thus be allowed to move radially outward to be at least partially received into the reliefs 924 of the outer collar 918, allowing the locking collar 904 and protrusions 912 to move distally past the retaining members 920 and the sheath 900 to be removed from the sheath connector device 914 and the instrument.

Figure 10A:
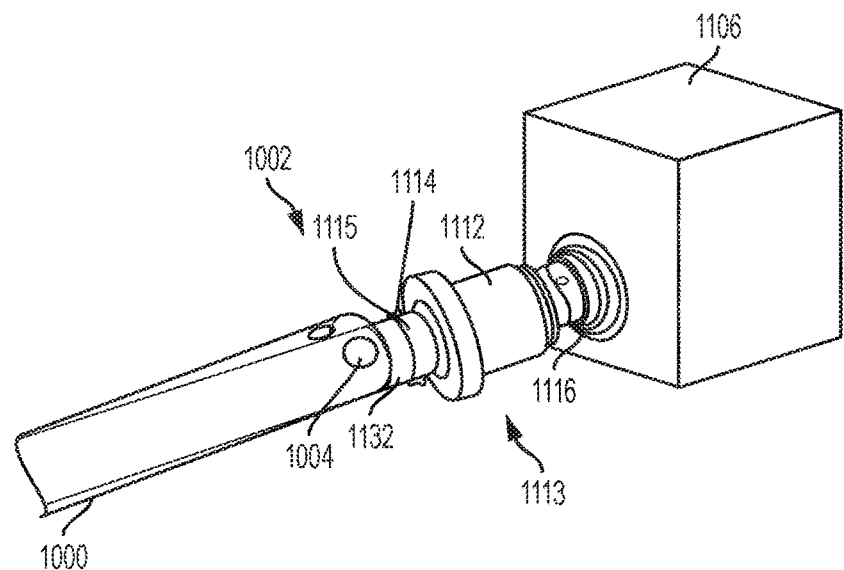
FIG. 10A is a perspective view of a sheath and an instrument according to another exemplary embodiment.
Figure 10B:
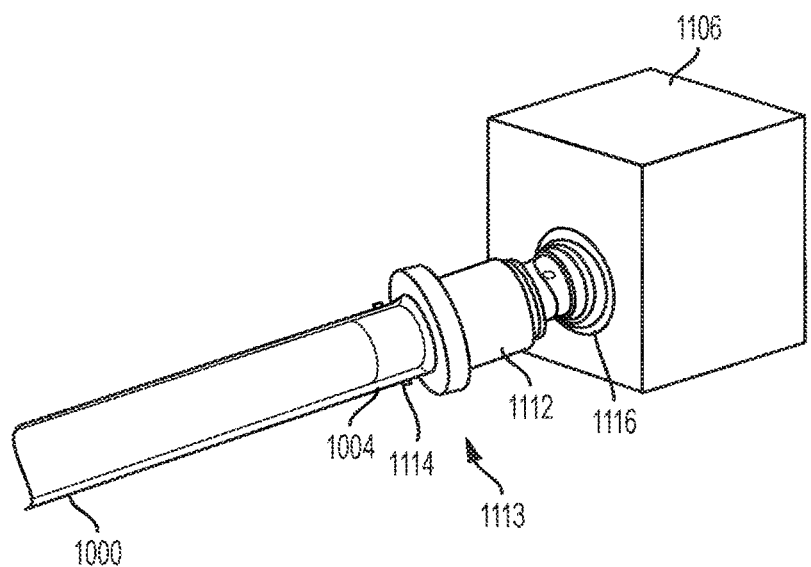
FIG. 10B is a perspective view of the sheath and instrument of FIG. 10A in an assembled configuration.

Referring now to FIG. 10A, another exemplary embodiment of a sheath 1000 and a corresponding sheath connector portion 1113 of an instrument 1130 is shown, with the sheath being a tubular sleeve having features configured to be engaged with the sheath connector portion 1113 of the instrument. The sheath 1000 includes a proximal end portion 1002 with female features 1004, such as holes, recesses, or other negative relief features on the lateral wall and at least through an outer surface, a plurality of which may be circumferentially spaced around a perimeter of the proximal end portion 1002. The sheath connector portion 1113 of the instrument may be positioned at a junction where the instrument shaft 1132 connects to the instrument transmission housing 1106. The sheath connector portion 1113 can comprise an inner collar 1115 configured to be received within the proximal end portion 1002 of the sheath 1000. The inner collar 1115 includes one or more male features 1114, such as, for example barbs or other similar protrusions, extending radially outwardly from an outer surface of the inner collar 1115. The male features 1114 are positioned and configured to fit within female features 1004 of the sheath 1000. The sheath connector portion 1113 further comprises an outer collar 1112 biased in a distal position by a biasing device 1116, such as, for example, a compression spring, or other biasing element. The collar 1112 is positioned to at least partially cover the male features 1114 when the biasing device 1116 is in an extended position forcing the collar 1112 in the distal position shown in FIG. 10B.

To install the sheath 1000, the collar 1112 is retracted in a proximal direction relative to the instrument, e.g., toward the instrument transmission housing 1106. In this position of the collar 1112, the sheath 1000 can be slid over the male features 1114 and can be rotated, if needed, until the holes 1004 are aligned with and receive one or more of the male features 1114, respectively. Releasing the collar 1112 then moves the collar 1112 over the male features 1114 to lock the connector portion 1113 and sheath 1000 together and to protect against disengagement of the male features 1114 with the sheath. In this way, the sheath 1000 is assembled to the instrument and prevented from being moved laterally and axially relative to the instrument shaft 1032.

In various exemplary embodiments described and shown herein, the sheath connector portion of the instruments are positioned at a juncture where the instrument shaft extends from a transmission housing, thereby allowing the sheath sleeve to extend substantially the entire length of the instrument shaft. However, the present disclosure contemplates positioning a sheath connector portion at other locations along the instrument shaft, in which configurations, the sheath would not extend to cover the entire length of the instrument shaft.

Further, in various exemplary embodiments that rely on an engagement of complementary retention features provided on the sheath and/or on the instrument, those of ordinary skill in the art would appreciate that modifications to the number and arrangement of those features may be altered as desired, for example, based on factors including, but not limited to, ease of installation of a sheath on an instrument, ease of manufacturing, desired retention forces tending to prevent rotation and/or axial movement of the sheath relative to an instrument in the assembled configuration, etc. By way of example, various exemplary embodiments include complementary and engageable male and female features. Persons having ordinary skill in the art would appreciate that the locations of the male and female features could be reversed on the various components with appropriate modification without departing from the scope of the present disclosure.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A medical instrument assembly comprising:
   a medical instrument comprising an instrument shaft and a sheath connector portion, the instrument shaft having a distal end portion configured to be introduced to a surgical site;
   a sheath sleeve configured to at least partially cover the instrument shaft, the sheath sleeve comprising a proximal end portion and a distal end portion; and
   a sheath sleeve retention mechanism located at the proximal end portion of the sheath sleeve,
   wherein the sheath connector portion comprises an engagement feature extending radially outwardly relative to the instrument shaft,
   wherein the sheath sleeve retention mechanism comprises a locking feature moveable between at least a first position and a second position,
   wherein in the first position of the locking feature, the locking feature is engaged with the engagement feature to retain the sheath sleeve in position on the instrument shaft, and
   in the second position of the locking feature, the locking feature is disengaged from the engagement feature and the sheath sleeve is removable from the instrument shaft.

2. The medical instrument assembly of claim 1, wherein: the distal end portion of the sheath sleeve is configured to be positioned proximate the distal end portion of the instrument shaft in the first position of the locking feature.

3. The medical instrument assembly of claim 1, wherein the sheath sleeve retention mechanism is attached to the proximal end portion of the sheath sleeve.

4. The medical instrument assembly of claim 3, wherein the sheath sleeve retention mechanism is bonded to the proximal end portion of the sheath sleeve with an adhesive.

5. The medical instrument assembly of claim 3, wherein the sheath sleeve retention mechanism is fused to the proximal end portion of the sheath sleeve.

6. The medical instrument assembly of claim 3, wherein the sheath sleeve retention mechanism is mechanically fastened to the proximal end portion of the sheath sleeve.

7. The medical instrument assembly of claim 6,
   wherein the sheath sleeve retention mechanism comprises:
   an inner retention mechanism part; and
   an outer retention mechanism part, and wherein the sheath sleeve is configured to be clamped between the inner retention mechanism part and the outer retention mechanism part.

8. The medical instrument assembly of claim 1, wherein the sheath sleeve retention mechanism comprises retention features formed in the sheath sleeve.

9. The medical instrument assembly of claim 1, wherein the locking feature comprises one or more resilient members deflectable from the first position to the second position.

10. The medical instrument assembly of claim 9, wherein:
the instrument shaft is configured to be inserted into the sheath sleeve and the sheath sleeve moved proximally over the instrument shaft to an assembled configuration of the sheath sleeve and instrument shaft; and
the engagement feature comprises a ramped outer surface profile configured to deflect the one or more resilient members of the locking feature around the engagement feature as the sheath sleeve retention mechanism is moved over the sheath connector portion to the first position of the locking feature.

11. The medical instrument assembly of claim 10, wherein the engagement feature defines a shoulder configured to abut the one or more resilient members in the second position of the locking feature.

12. The medical instrument assembly of claim 9, wherein the locking feature is deflectable to the second position in response to a radially inward directed force applied on a portion of the locking feature.

13. The medical instrument assembly of claim 12, wherein the locking feature comprises a pair of force application surfaces positioned at opposite lateral sides of the locking feature and configured to receive the radially inward directed force.

14. A sheath assembly for a medical instrument shaft, the sheath assembly comprising:
a sheath sleeve configured to receive the medical instrument shaft; and
a sheath retention mechanism comprising:
a sheath attachment portion configured to attach the sheath retention mechanism to the sheath sleeve, and
a locking collar extending from the sheath attachment portion, the locking collar comprising one or more resilient members,
wherein the one or more resilient members are configured to deflect radially outward from a first, undeflected position to a second, deflected position in response to a radially inward directed force applied to a portion of the locking collar,
wherein, in the first, undeflected position, the one or more resilient members are a first distance from a central axis of the sheath sleeve,
wherein in the second, deflected position, the one or more resilient members are a second distance from the central axis of the sheath sleeve, the second distance being greater than the first distance, and
wherein, in an attached state of the sheath retention mechanism to the sheath sleeve, the sheath retention mechanism and the sheath sleeve permit insertion of the medical instrument shaft through the sheath retention mechanism and the sheath sleeve.

15. The sheath assembly of claim 14, wherein the locking collar further comprises a pair of force application surfaces positioned at opposite lateral sides of the locking collar, the pair of force application surfaces being configured to receive the radially inward directed force.

16. The sheath assembly of claim 14, wherein the one or more resilient members comprise first and second resilient members laterally opposite one another on the locking collar.

17. The sheath assembly of claim 14, wherein the locking collar has a first interior transverse cross-section in the first, undeflected position and a second interior transverse cross-section, differing from the first interior transverse cross-section, in the second, deflected position.

18. The sheath assembly of claim 17, wherein one of the first interior transverse cross-section and the second interior transverse cross-section is circular and the other of the first interior transverse cross section and the second interior transverse cross section is elongated.

19. The sheath assembly of claim 14, wherein the sheath retention mechanism further comprises one or more longitudinally extending splines on an inner surface of the sheath attachment portion, the one or more longitudinally extending splines configured to interact with one or more complementary features of the medical instrument shaft to prevent rotation of the sheath sleeve relative to the medical instrument shaft.

20. The sheath assembly of claim 14, wherein in the first position of the resilient members, the resilient members are configured to engage a connector portion of the medical instrument shaft.

* * * * *